(12) United States Patent
Schneider et al.

(10) Patent No.: US 8,337,382 B2
(45) Date of Patent: Dec. 25, 2012

(54) RADIOSURGICAL NEUROMODULATION DEVICES, SYSTEMS, AND METHODS FOR TREATMENT OF BEHAVIORAL DISORDERS BY EXTERNAL APPLICATION OF IONIZING RADIATION

(75) Inventors: M. Bret Schneider, Portola Valley, CA (US); John R. Adler, Jr., Stanford, CA (US); Doyle John Borchers, III, Palo Alto, CA (US); Michele Borchers, legal representative, Palo Alto, CA (US)

(73) Assignees: John R. Adler, Jr., Stanford, CA (US); M. Bret Schneider, Portola Valley, CA (US)

( * ) Notice: Subject to any disclaimer, the term of this patent is extended or adjusted under 35 U.S.C. 154(b) by 1091 days.

(21) Appl. No.: 12/261,347

(22) Filed: Oct. 30, 2008

(65) Prior Publication Data
US 2009/0114849 A1 May 7, 2009

Related U.S. Application Data

(60) Provisional application No. 60/984,636, filed on Nov. 1, 2007.

(51) Int. Cl.
*A61N 5/10* (2006.01)
(52) U.S. Cl. .......................................................... 600/1
(58) Field of Classification Search .................. 600/1, 2; 250/492.1, 492.3
See application file for complete search history.

(56) References Cited

U.S. PATENT DOCUMENTS

| | | | | |
|---|---|---|---|---|
| 2,638,554 A | * | 5/1953 | Bartow et al. ................. | 378/147 |
| 5,748,700 A | * | 5/1998 | Shepherd et al. ............... | 378/65 |
| 5,997,176 A | * | 12/1999 | Fairleigh ....................... | 378/196 |
| 6,501,981 B1 | * | 12/2002 | Schweikard et al. .......... | 600/427 |
| 7,085,347 B2 | * | 8/2006 | Mihara et al. .................. | 378/65 |
| 2002/0074559 A1 | * | 6/2002 | Dowling et al. ............... | 257/99 |

OTHER PUBLICATIONS

Pellmar TC, Schauer DA, and Zeman GH. Time- and Dose-Dependent Changes in Neuronal ACtivity Produced by X Radiation in Brain Slices. Radiaton Research 1990; 122: 209-214.*

Lewine RRJ, Hudgins P, Brown F, Caudle J, Risch SC. Differences in Qualitative Brain Morphology Fidnings in Schizophrenia, Major Depression, Bipolar Disorder, and Normal Volunteers. Schizophrenia Research 1995; 15: 253-259.*

(Continued)

*Primary Examiner* — Charles A Marmor, II
*Assistant Examiner* — Joshua D Lannu
(74) *Attorney, Agent, or Firm* — Kilpatrick Townsend & Stockton LLP

(57) ABSTRACT

Radiosurgical techniques and systems treat behavioral disorders (such as depression, Obsessive-Compulsive Disorder ("OCD"), addiction, hyperphagia, and the like) by directing radiation from outside the patient toward a target tissue within the patient's brain, typically without imposing surgical trauma. The target will often be included in a neural circuit associated with the behavioral disorder. A cellularly sublethal dose of the radiation may be applied and the radiation can mitigate the behavioral disorder, obesity, or the like, by modulating the level of neural activity within the target and in associated tissues. Hypersensitive and/or hyperactive neuronal tissue may be targeted, with the radiation downwardly modulating hyperactive neuronal activity. By down-regulating the activity of a target that normally exerts negative feedback or a limiting effect on a relevant neural circuit, the activity of the circuit may be increased.

49 Claims, 12 Drawing Sheets

OTHER PUBLICATIONS

Pizzagali D, Pascual-Marqui, RD, Nitschke JB, Oakes TR, Larson CL, Abercrombie HC, Schaefer SM, Koger JV, Benca RM, and Davidson RJ. Anterior Cingulate Activity as a Predictor of Degree of Treatment Response in Major Depression: Evidence from Brain Electrical Tomography Analysis. American Journal of Psychiatry 2001; 158: 405-415.*

Tracy AL, Jarrard LE, Davidson TL. The Hippocampus and Motivation Revisited: Appetite and Activity. Behavioral Brain Research 2001; 127: 13-23.*

Maltby N, Tolin DF, Worhunsky P, O'Keefe TM, Kiehl KA. Dysfunctional Action Monitoring Hyperactivates Frontal-striatal Circuits in Obsessive-compulsive Disorder: an Event-related fMRI study. Neuroimage 2005; 24:495-503.*

Hyman Se and Malenka RC. Addiciton and the Brain: The Neurobiology of Compulsion and Its Persistence. Nature Reviews: Neuroscience 2001; 2: 695-703.*

Kandel ER, Schwartz JH, and Jessell TM. Principles of Neural Science 4th Edition. New York: McGraw-Hill Companies Inc, 2000. 1002-1006. Print.*

\* cited by examiner

Hunger Circuit and Obesity Treatment

RADIOSURGICAL NEUROMODULATION DEVICES, SYSTEMS, AND METHODS FOR TREATMENT OF BEHAVIORAL DISORDERS BY EXTERNAL APPLICATION OF IONIZING RADIATION

CROSS-REFERENCES TO RELATED APPLICATIONS

The present application claims the benefit under 35 USC 119(e) of U.S. Provisional Application No. 60/984,636 filed Nov. 1, 2007; the full disclosure of which is incorporated herein by reference in its entirety.

BACKGROUND OF THE INVENTION

The present invention is generally directed to medical (and in many cases, more specifically to neurological) treatment devices, systems, and methods. In exemplary embodiments, the invention provides radiosurgical treatment methods and systems for directing ionizing radiation toward a target tissue within a brain of a patient so as to treat psychiatric conditions, and particularly to treat behavioral disorders (such as depression, Obsessive-Compulsive Disorder ("OCD"), addiction, hyperphagia, and the like), and/or to treat obesity. The dose of radiation will often be sub-lethal so that the tissue within the target need not undergo frank cell death, with efficacy often instead being provided via radiomodulation of neural activity.

Behavioral disorders are neurologic and psychiatric conditions that stem from defective regulation of certain brain regions. Patients that suffer from behavioral disorders often exhibit abnormal neural activity along a particular neural circuit within the brain. Typically, areas within the neural circuits of the brain of a behavioral disorder patient are either over-active or under-active, even though the cells of the tissue appear normal. This class of pathology contrasts with structural disorders, in which there is something morphologically or identifiably and physically abnormal with a tissue, such as an injury or a cancerous tumor. Nonetheless, the impact of behavioral disorders, including depression, OCD, addiction, and the like, can be devastating on the lives of patients and their families.

In neurology and psychiatry, behavioral disorders are most often treated with medications. Unfortunately, these medications can often be non-specific as to where they exert effects within the body. Hence, medications for treatment of behavioral disorders often produce undesirable side effects.

Attempts are being made to treat behavioral disorders by surgical implantation of treatment devices. These surgical implants typically include stimulating electrodes driven by a pacemaker-like pulse generator unit. For example, abnormal neuronal activity associated with intractable depression may be inhibited by continuously applying localized electrical current using a process called deep brain stimulation. Unfortunately, deep brain stimulation generally involves the invasive placement of electrodes into deep brain structures, along with the subcutaneous implantation of an electrical generator with batteries. Such approaches, however, are expensive, and are generally accompanied by risks associated with the surgery, particularly with the risks associated with surgically accessing tissues of the brain for implantation of the electrodes such as bleeding and infection. These approaches can also suffer from device-related risks, including device failure, battery-life limits, and the like.

A variety of both historical and modern techniques seek to treat patients by effectively killing cells within selected areas of the brain. Surgical techniques have been developed that intentionally kill or ablate specific regions of the brain using a variety of devices and energy forms. For example, radiation is a widely used method for inducing cell death and effectively destroying tissue within the brain. Radiation is primarily applied to tissues of the brain to treat benign and malignant tumors. The clinical practice of irradiation to produce selective cell death in tumors generally makes use of computerized systems that seek to minimize injury to adjacent normal anatomy. The biologic effects of radiation are largely ascribed to lethal chromosomal injury which results in disruption of the normal cell cycle. Non-chromosomal, i.e. epigenetic, pathways of cell injury are also believed to play a role in cellular death under some circumstances.

While inducing necrosis of selected tissues of the brain can be well worthwhile to halt growth of a malignant tumor or the like, there can be significant and even debilitating side effects, particularly when the tissues targeted for treatment are associated with higher cognitive functions. For example, targeting of apparently healthy tissues of the hyperactive or hypersensitive neural circuits associated with depression, addiction, OCD, or other behavioral disorders for cellularly lethal doses of radiation might effectively treat the disorder, but may significantly degrade cognitive abilities, induce neurological side-effects, and impact quality of life of the patient.

In addition to currently recognized neural circuits associated with behavioral disorders, there is an increasing awareness that abnormal neural activity within the neural circuits of the brain may be associated with a variety of deleterious behavior patterns. For example, while obesity is not uniformly recognized as a class of psychiatric behavioral disorder, there is increasing understanding that hyperphagia (excessive appetite and consumption of food) can be associated with excessive activity in an associated neural circuit. Similar deleterious behavior patterns and their associated anatomical structures within the brain are likely to be identified in the future.

In light of the above, it would generally be desirable to provide improved medical systems, devices, and methods, particularly for treatment of behavioral disorders, obesity, and the like. It would further be desirable if these improved treatment techniques could help mitigate the debilitating effects of behavioral disorders without imposing excessive surgical trauma on the patient, and without having to damage or kill neural tissues throughout an area that might result in loss of significant cognitive, emotional, or physical functionality to the patient. It would be particularly desirable if these benefits could be provided at reasonable costs by modifying existing treatment infrastructure and technologies.

BRIEF SUMMARY OF THE INVENTION

The present invention generally provides improved medical systems, devices, and methods. Exemplary embodiments of the invention provide improved radiosurgical techniques and systems, particularly for treatment of behavioral disorders (such as depression, Obsessive-Compulsive Disorder ("OCD"), addiction, hyperphagia, and the like). Related embodiments may be employed for treatment of obesity. Advantageously, radiation can be directed from a radiation source outside the patient toward a target tissue deep within the patient's brain using a stereotactic radiosurgical platform, typically without having to impose the surgical trauma associated with accessing deep brain tissues. The target will often be included in a neural circuit associated with the behavioral disorder. Rather than applying sufficient radiation to kill the neural tissue within the target, a cellularly sub-lethal dose of the radiation may be applied. Without imposing frank cell death throughout the target, the radiation can mitigate the behavioral disorder, obesity, or the like, often by modulating the level of neural activity within the target and in associated tissues. Hypersensitive and/or hyperactive neuronal tissue may be targeted, with the radiation downwardly modulating hyperactive neuronal activity. Additionally, by down-regulating the activity of a target that normally exerts negative feedback or a limiting effect on a relevant neural circuit, the activity of the circuit may be increased.

In a first aspect, the invention provides a method for treating a psychiatric behavioral disorder or hyperphagia of a patient. The disorder or hyperphagia is associated with a level of neuronal activity in a neural circuit within a brain of the patient, and provokes deleterious volitional behavior by the patient. The method comprises transmitting a sub-lethal quantity of ionizing radiation from outside the patient into a target within the brain of the patient so as to alter the level of neuronal activity in the neural circuit. By altering the activity level, the behavioral disorder or hyperphagia is mitigated.

The neural circuit will typically comprise a recognized behavioral neural circuit that is known to be associated with the behavioral disorder or hyperphagia. A variety of such neural circuits are now known, and more are being developed through the use of imaging techniques which can indicate local neuronal activity levels within the tissues of the brain. Although the overall functioning of the neural circuit is often abnormal prior to treatment of a behavioral disorder patient (for example, with abnormally excessive neuronal activities in some or all of the neural circuit) the neural tissue within the target will often be morphologically normal prior to the treatment, so that the treatment is directed at what may be effectively healthy tissue. Nonetheless, by selecting an appropriate target within the neural circuit, and by applying a quantity of radiation that is sufficient to decrease the level of neuronal activity within the targeted neural tissue (but which is insufficient to generally kill the tissue of the target), the level of overall activity of the neural circuit may be safely and effectively decreased without excessively (or even significantly) impairing the higher cognitive, emotional, and/or physical functioning of the patient. Alternatively, where the neural tissue within the target down-regulates the level of neuronal activity within at least a portion of the neural circuit, the radiation may decrease activity in the neural tissue and lead to an increase in the level of neuronal activity within some or all of the neural circuit.

Advantageously, the target may comprise one or more discrete tissue structure of the brain having anatomical boundaries. The ionizing radiation can be transmitted from a radiation source as a plurality of radiation beams, and the radiation beams can be planned so that radiation outside the anatomical boundaries drops off sufficiently to inhibit collateral damage to adjacent neural tissues and preserve cognitive function. As the dosage of radiation even within the target neural tissue is generally cellularly sub-lethal, necrosis outside the anatomical boundaries of the target may be quite limited or even negligible. The volume of the target will often be quite small, the target typically having a volume of less than 0.5 cc, often having a volume of less than 0.125 cc, and in some cases having a volume of less than 0.06 cc. To facilitate treatment of these small tissue volumes and minimize collateral tissue damage, some or all of the radiation beams may be smaller in cross-section than those used in standard tumor-treatment stereotactic radiosurgery. For example, at least some of the radiation beams may be collimated to a beam cross-sectional size of less than 3 mm.

Before treatment, a medical professional will typically clinically determine that the behavioral disorder falls within an accepted psychiatric standard. Such standards may, for example, comprise one or more of those included within the Diagnostic and Statistical Manual of Mental Disorders, 4th edition ("DSM IV"). The target may be identified using an accepted psychiatric neural circuit associated with the behavioral disorder of the patient. The target may also be identified, verified, and/or tailored by imaging localized neuronal activity levels along the neural circuit of the patient. Hence, for example, once a clinical diagnosis is established and the patient otherwise meets the patient selection criteria, hyperactivity of a candidate neural circuit known to be associated with the disorder can verify that the treatment is appropriate, and the radiation beam trajectories can be planned based on the anatomical borders of the discrete tissues of the particular patient. Imaging may also be performed an appropriate tissue response time after treatment and to verify that sufficient neuromodulation has been provided, to determine whether a follow-on treatment is appropriate, and/or to plan that follow-on treatment in a fractionated treatment regime. It may be advantageous to verify mitigation of the disorder after more than a month, and often after at least two months, as the changes in the level of neuronal activity may continue for at least a period of weeks or months after the radiation has been delivered to the target.

The sub-lethal quantity of radiation may depend at least in part on the volume of a discrete region of the target tissues. For example, the radiation dose for a single treatment may comprise about 60 Gy when the target has a volume of about 0.05 cc (and more specifically when the target has a volume of about 0.054 cc). In contrast, the radiation dose may be significantly less than about 60 Gy when the target has a size of significantly more than about 0.05 cc, and/or more than about 60 Gy when the target has a size of significantly less than about 0.05 cc.

A variety of functional disorders and other conditions may be treated by directing the radiation to one or more appropriate target(s). One preferred treatment may mitigate a behavioral disorder by targeting Cg25, though a variety of alternative targets may also be selected. For example, depression may be mitigated by targeting a rostral anterior cingulate (rCg24a); a dorsal anterior cingulate (dCg24); Cg 32; and/or a subgenual cingulate (sCg25 or Cg25). Obsessive-Compulsive Disorder (OCD) may be treated by targeting an internal capsule; BA32; Cg24; a ventral PFC, and/or a dorsal anterior cingulate. Addiction may be treated by targeting an insula; a genu of the anterior cingulate (BA32); an arcuate nucleus of a medial hypothalamus; an anterior cingulate cortex or Brodmann's area 24; an orbitofrontal cortex; a medial prefrontal cortex; a dorsal anterior cingulate; an anterior limb of an internal capsule; a nucleus accumbens; and/or a neural circuit connection between the ventral tegmentum and the nucleus accumbens. Hyperphagia and/or obesity may be mitigated by targeting a lateral nucleus of a hypothalamus and/or bilateral nuclei of the hypothalamus. These and other conditions may advantageously be mitigated by transmitting the radiation from outside the patient, through a skull and into the brain along beam paths directed from varying directions so as to intersect with the target, often without accessing the target and/or the neural circuit.

In another aspect, the invention provides a system for treating a psychiatric behavioral disorder or hyperphagia of a patient. The disorder or hyperphagia can be associated with a level of neuronal activity in a neural circuit within a brain of the patient, and may provoke deleterious volitional behavior by the patient. The system comprises a source for transmitting ionizing radiation, and a processing system coupled to the source. The processing system can be configured to effect transmission of a plurality of beams of the radiation from the source into a target within the brain of the patient. The processing system can plan the beams so that the radiation within the target has a sub-lethal quantity, but is sufficient to alter the level of neuronal activity in the neural circuit such that the behavioral disorder or hyperphagia is mitigated.

The processing system typically comprises software, with the software including machine-readable code embodying instructions for planning transmission of the plurality of beams. The software may, in response to input command signals received by an input, transmit signals so as to effect a desired positioning of the radiation beams relative to the target, the signals typically comprising drive signals that effect movement of the source, the patient, or both.

The system may include a neural circuit image capture device coupled to the processing system. The image capture device may, in use, generate image data that includes localized neuronal activity levels along the neural circuit in the brain of the patient, the image capture device coupled to the processing system. Suitable image capture devices may include a positron emission tomography (PET) system, a single photon emission tomography (SPECT) system, and/or functional magnetic resonance imaging (fMRI) system.

In some embodiments, the source may comprise a linear accelerator. The processing system can be configured to generate a sequence of beams, and a robot may be coupled to the processing system and support the source. The robot may re-position the source and orient sequential beams toward the target tissue. One or more registration imaging system may be oriented to obtain patient registration images of the patient during treatment. The registration imaging system will typically be coupled to the processing system, and the processing system may align the beams with the target (often in three dimensions) in response to registration signals from the registration image system. In alternative embodiments, the source may comprise a plurality of cobalt 60 sources distributed generally spherically, with an associated plurality of collimators oriented generally radially inwardly so that at least some of the beams are simultaneously directed toward the target.

DETAILED DESCRIPTION OF THE INVENTION

Figure 1:
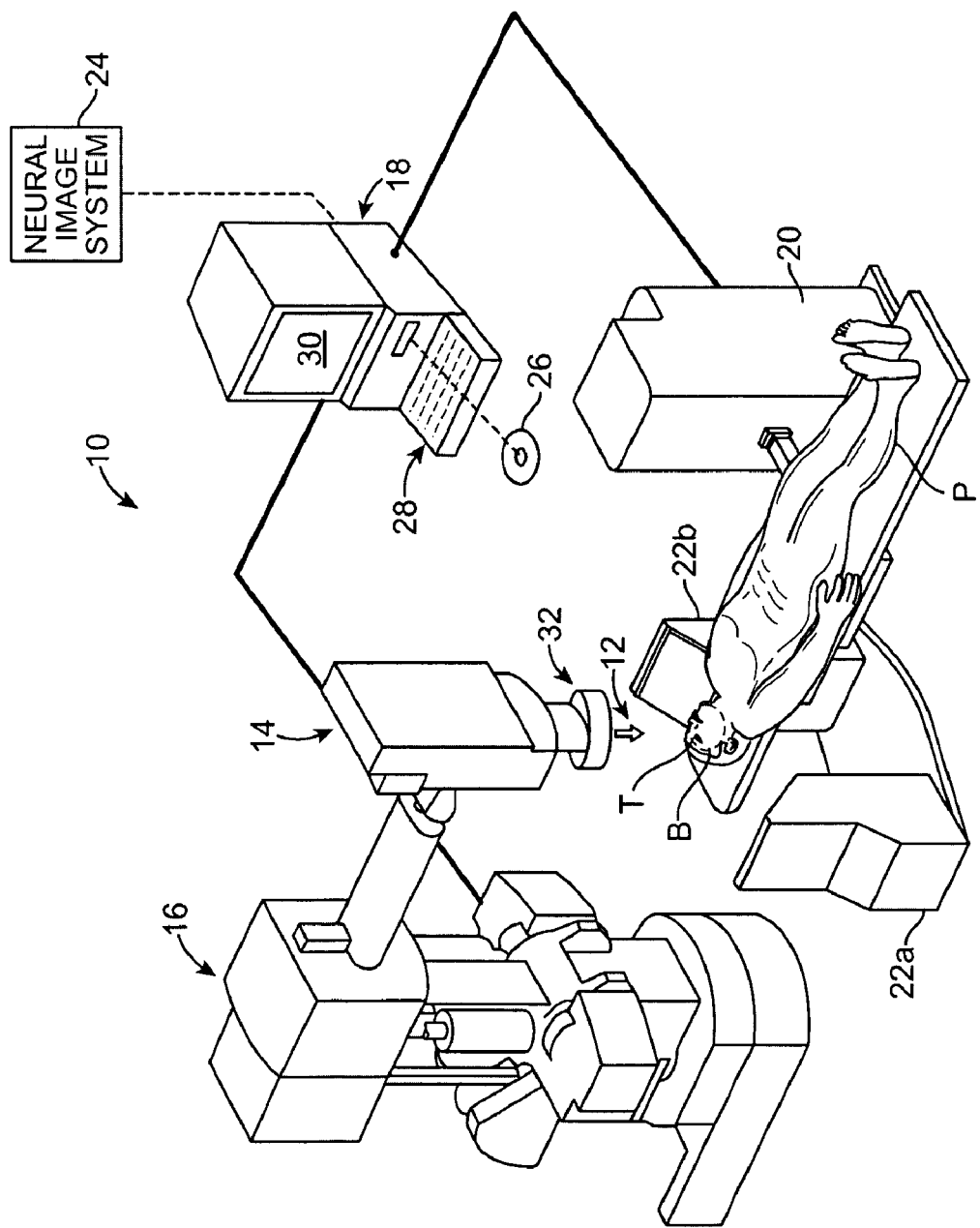
FIG. 1 schematically illustrates components of a robotic stereotactic radiosurgical system and an associated method for applying cellularly sub-lethal ionizing radiation to a target within a brain of a patient so as to treat a behavioral disorder, hyperphagia, obesity, or the like, according to embodiments of the invention.

The present invention generally provides improved medical systems, devices, and methods. Exemplary embodiments of the invention provide improved radiosurgical techniques and systems, particularly for treatment of behavioral disorders, including depression, Obsessive-Compulsive Disorder ("OCD"), and addiction. Treatments are also provided for additional medical and/or psychiatric conditions, particularly those that are associated with neural activity levels in identifiable neural circuits of the brain, including hyperphagia and obesity. As treatments described herein may rely on the delivery of radiation transmitted from a source outside the patient, through the skull and any intervening tissues, and concentrated within the target, these treatments may optionally avoid the surgical trauma associated with accessing deep brain tissues. Alternative embodiments could, however, combine non-invasive methodologies described herein with minimally invasive or even traditional open surgical techniques. While some embodiments might employ sufficient radiation to result in significant necrosis within (or even throughout) the target, exemplary embodiments will generally limit the radiation to cellularly sub-lethal dosages, so that there will be little or no necrosis. Frank cell death will typically be limited or absent, but the radiation will modulate, and typically decrease the overall level of neuronal activity within the target. By down-regulating the activity of a target that normally exerts negative feedback or a limiting effect on another neural tissue, neural activity may alternatively be increased.

Advances in brain imaging, especially those involving MRI and PET, are starting to unravel a spectrum of psychiatric behavioral disorders. Such imaging modalities have implicated a number of specific anatomic regions as being involved in some pathologic brain conditions. The altered imaging characteristics of these regions may allow physicians to visualize the brain pathology that underlies diseases such as depression and addiction. In a more specific example, treatment-resistant depression may particularly benefit from the treatments described herein. Increased metabolic activity in Brodmann's Area 25 may correlate well with clinical depression. This anatomical structure may also interact with a variety of other anatomical structures having altered activity levels in many patients suffering from depression, with the interrelated tissue structures generally defining an abnormally functioning neural circuit model. Using these imaging techniques and/or the neural circuits that have been identified for specific behavioral disorders, the effects of therapy for those behavioral disorders may be monitored by means of MRI and PET.

The neural tissues targeted for the radiation treatments described herein will often be included within an abnormally functioning high-level neural circuit of the patient's brain. In some cases, the target may not be in the neural circuit itself, but may functionally interact with a tissue included in the neural circuit, with activity in the target effectively up-regulating activity A variety of neural circuits are known to be associated with individual behavioral disorders. Exemplary neural circuits associated with depression, Obsessive-Compulsive Disorder ("OCD"), addiction, and obesity are described hereinbelow, and these exemplary circuits may be used to identify appropriate tissues to target for patient having these disorders or conditions. The invention is not, however, limited to the specific behavioral disorders and/or neural circuits provided herein, as additional and more refined neural circuits are (and will continue to be) developed.

In some embodiments, the overall neural circuits associated with the disorder may also, at least in part, be determined, refined, and/or verified by appropriate imaging of a specific candidate patient suffering from a disorder. In some embodiments, hyperactivity along a neural circuit may be seen in a patient having an acute or ongoing episode by imaging the neural tissues with imaging modalities that indicate localized neuronal activity levels. For example, by stimulating an addict with appropriate drug paraphernalia images or the like, the neuronal activity may be imaged and measured along an addiction neural circuit to verify that particular neural circuit model is applicable to the patient, to verify that a candidate target neural tissue becomes hyperactive during the episode, and to tailor the target shape to the anatomical boundaries of the patient's brain physiology. Treatments may be fractionated, with follow-up clinical diagnosis and/or imaging after at least one treatment to determine whether additional modulation of the same target is appropriate, to select additional targets, or to determine that treatments can be suspended or terminated. More directly, treatments may be repeated if inadequate clinical response has been obtained.

Radiosurgery is an established method for using intense, highly accurate irradiation to non-invasively ablate (killing or otherwise destroying) abnormal tissue within the body, for example, brain tumors. Examples of radiosurgical platforms include the Cyberknife (Accuray, Inc., Santa Clara, Calif.), the Gamma Knife (Elekta, Stockholm Sweden), and the Trilogy System (Varian, Palo Alto, Calif.). These or other commercially available radiosurgery systems may be modified to take advantage of the inventions described herein, or specialized radiosurgical systems for treatment of behavioral disorders may be employed.

The present invention often applies radiosurgical platforms for neuromodulation rather than ablation. Radiomodulation ("RM") (also referred to herein as radiosurgical neuromodulation) encompasses the use of non-necrosing stereotactic radiosurgery for the down-regulation of selected neural structures. Advantageously, small and strategically important neuronal regions may be treated with dosages of radiation that are sufficiently low to leave their tissues alive and functional, but are sufficiently high to make them less reactive, and less able to trigger action potentials, i.e. precipitate deep-brain neuromodulation clinical response. A variety of data may be applied to identify appropriate dosages to alter brain function without frank cell death. Irradiation of the entire brain of patients produces long term cognitive decline without producing clear evidence of tissue necrosis, and may produce other undesired emotional and physically-manifested neurological symptoms. Decreased neuronal excitability within hippocampal slices of pig brain has been revealed by in vitro evidence. Moreover, treatment of trigeminal neuralgia with radiosurgery has been found to provide symptom relief that does not correlate temporally with facial numbness. In fact, treatment of more than 100 patients with refractory trigeminal neuralgia has shown that the complete remission of pain occurs in a setting of essentially normal facial sensation. Dose application rates may alter the total dosages to achieve a desired result. At dose rates of 20 Gy per minute, synaptic damage (lessened ability to transmit excitation to another neuron) may occur when a 50 Gy total dose had accumulated. Doses of 75 Gy and greater may provide both synaptic and postsynaptic damage (lessened ability of a downstream neuron to produce an action potential). At slower delivery rates of about 5 Gy/min, however, a total dose of 100 Gy or more may be applied to induce synaptic impairment, while post-synaptic impairment may not be dose-rate dependent. Appropriate dosages may also vary with the inverse of a volume or size of the target. One exemplary treatment of a target volume of about 3 mm by about 3 mm by about 6 mm (about 0.054 cc) will employ a dosage of about 60 Gy to achieve RM; significantly larger target volumes may employ lower dosages; while smaller target volumes may employ significantly higher dosages.

While many embodiments do not rely on any particular mechanism or theory of operation, ionizing radiation may cause an inhibitory effect upon voltage-sensitive sodium channels in the brain. This may results in a state in which affected neurons remain chronically in a hyperpolarized state, which is resistant to depolarization. Radiation may also result in the thickening of blood vessel walls and narrowing of lumens, to the point of frank destruction of the microvasculature, leading to reduced blood delivery capacity within an irradiated area. These effects may be progressive over time after radiation exposure, reaching a steady state. Additionally, the blood-brain barrier may be disrupted by ionizing radiation, allowing release of neuromodulatory substances such as neurotensin, histamine and serotonin. Hence, moderate-dose radiation may alter neuronal and synaptic activity through mechanisms that change the functional characteristics of individual cells without killing those cells. By physiologically altering, but not destroying, discrete neural circuits, brain activity can be modulated.

Referring now to FIG. 1, an exemplary stereotactic radiosurgery system 10 for treatment of a behavioral disorder or hyperphagia of a patient P directs ionizing radiation 12 to a target T in a brain B of the patient. System 10 includes a linear accelerator 14 supported by a 6 degree of freedom robot 16, which allows the linear accelerator to be moved around the patient, so that radiation 12 can be directed to target T as a sequential series of beams that pass through different intermediate tissues from a variety of different orientations, thereby limiting the amount of radiation outside the target.

System 10 also includes a processing system 18 that is coupled to linear accelerator 14 to control transmission of radiation 12. Processing system 18 is also coupled to robot 16, and optionally to an automated patient support 20 to reposition radiation 12 relative to the patient P and target T. Processing system 18 may also be coupled to one or more imaging system(s) used for planning of the treatments, to imaging systems 22a and 22b used to register radiation beam 12 with target T in three dimensions and/or track patient movements during treatment. Registration imaging systems, the linear accelerator, the robot, and the patient support may be the same as or modified from commercially available robotic radiosurgical systems, including the CyberKnife radisurgical system. Additional or modified imaging structures and systems will often be coupled to processing system 18 so as to provide input for planning the treatment and the like, such as a neural activity imaging system 24.

To facilitate treatment of the relatively small volume discrete anatomical structures of the neural circuits, system 10 will typically include a collimator 32 which selectably narrows beam 12 to beam cross-sectional sizes of 3 mm or smaller, and in some embodiments to a cross-sectional size of 5 mm or smaller.

Processing system 18 may include some or all of the components of a commercially available computer system. Processing system 18 will, for example, typically includes at least one hardware processor circuit, which may communicate with a number of peripheral devices via a bus subsystem. These peripheral devices may include a memory system, and the memory will typically include a tangible storage media 26 embodying machine (i.e., computer) readable instructions for performing methods (including those described herein) and/or data. The memory may comprise a random access memory (RAM), a read only memory (ROM), a persistent (non-volatile) storage such as a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks including flash RAM.

In some embodiments, processing system 18 will comprise a proprietary structure, and will likely include a plurality of discrete processing circuits, with separation structures of the processing system being primarily used for planning treatments, analyzing neural images, controlling movement of robotic components of system 10, and the like. Alternatively, simpler systems might employ a single processor chip running a monolithic computer program and packaged with single input 28 and display 30. Hence, a wide variety of centralized or distributed data processing hardware and software architectures may be implemented, and the functionality described herein may be implemented in a variety of software and/or hardware modules distributed in different data processing structures and locations. Exemplary embodiments of the processing system 18 of system 10 may be provided by input to and modifications of the data processing and signal transmission systems of commercially available radiosurgery systems such as the CyberKnife™ robotic stereotactic system from Accuray, Inc.

Figure 2:
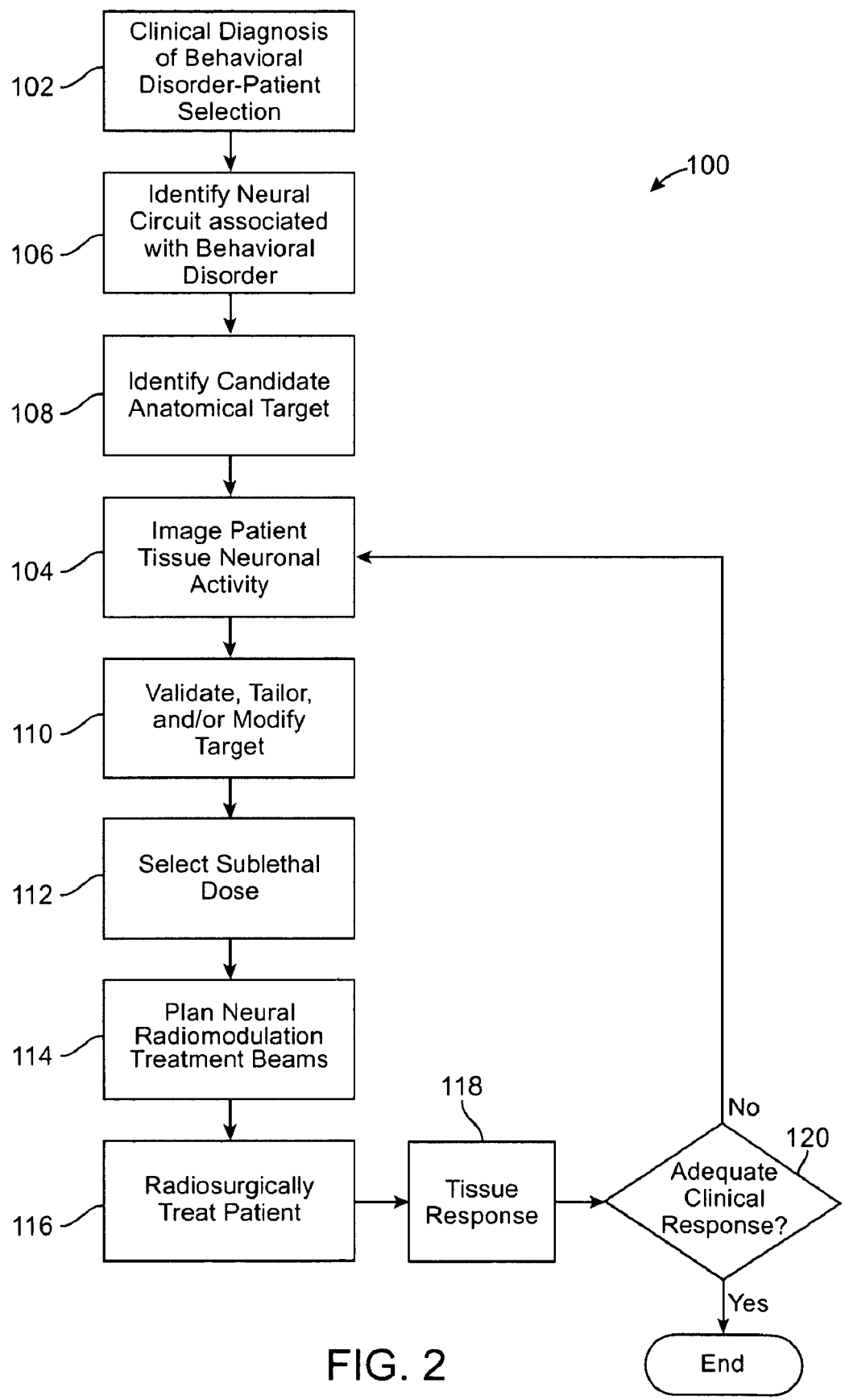
FIG. 2 is a flow chart schematically illustrating steps included in a method for treating a behavioral disorder, hyperphagia, or the like using the system of FIG. 1 or other radiosurgical systems.

Referring now to FIG. 2, an exemplary method 100 for treatment of a behavioral disorder, hyperphagia, obesity, and/or the like will often begin with the selection of an appropriate candidate patient. Such a patient will typically have a neuropsychiatric brain disorder for which there is reason to believe that one or more specific regions of the brain are overactive or hypermetabolic. This diagnosis may be accomplished via clinical judgment 102, and/or may be accomplished with the aid of functional brain imaging 104. In clinically diagnosing a behavioral disorder, a medical professional will typically clinically determine that the behavioral disorder falls within an accepted psychiatric standard. Such standards may, for example, comprise one or more of those included within the Diagnostic and Statistical Manual of Mental Disorders, 4th edition ("DSM IV"). Suitable imaging techniques for behavioral disorder diagnosis will generally indicate localized neuronal activity levels, with exemplary imaging systems optionally comprising positron emission tomography (PET), single photon emission tomography (SPECT) or functional magnetic resonance imaging (fMRI). Imaging of the patient's head preferably involves acquiring both a high resolution MRI scan of the patient's brain and a thin section CT scan of the same region.

Figure 3:
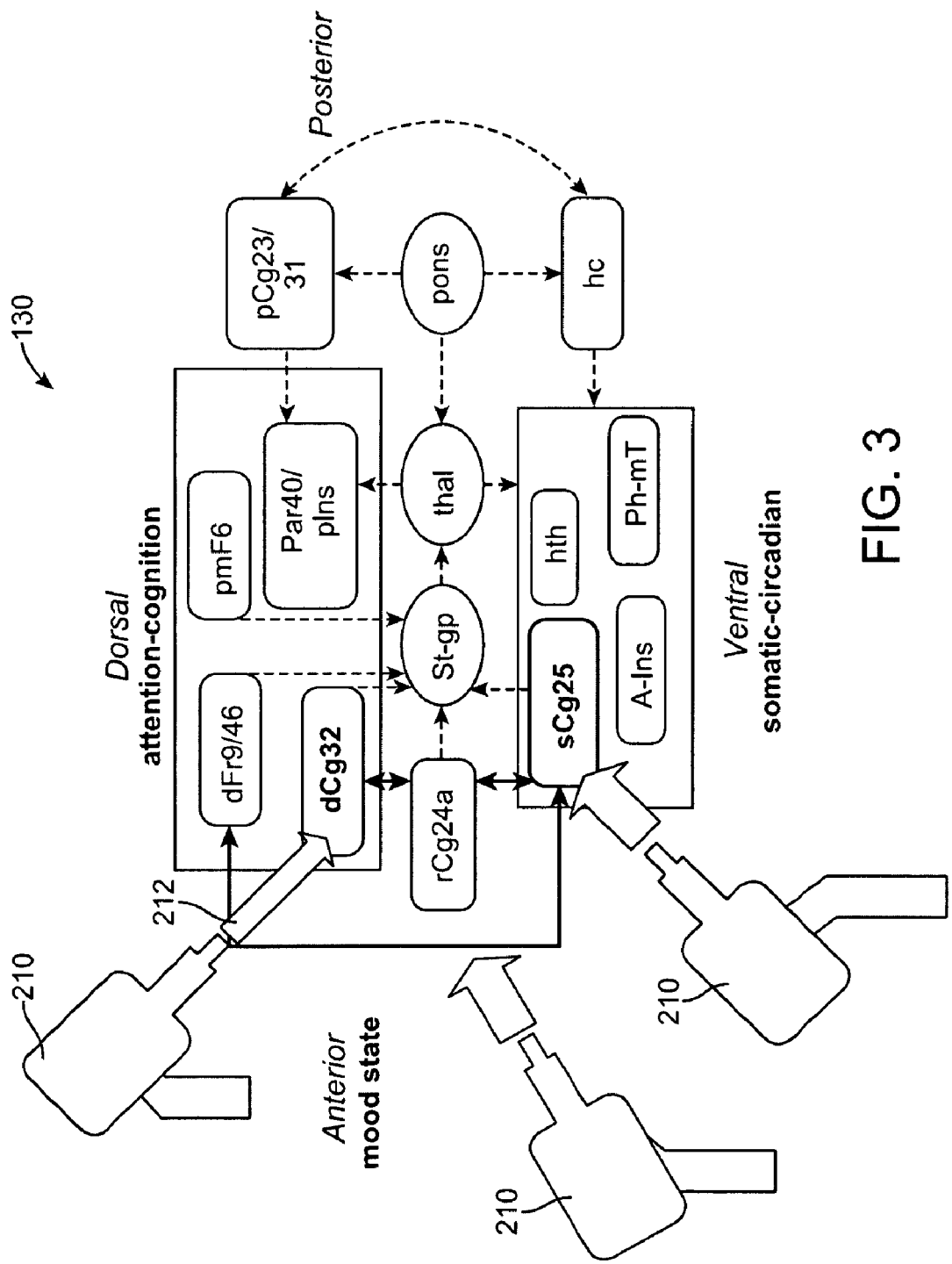
FIG. 3 schematically illustrates a neural circuit associated with depression, along with candidate tissues suitable for treatment according to embodiments of the invention.

Neural circuits associated with the behavioral disorder may be identified 106 before or after imaging 104. Suitable neural circuits may comprise neural circuit models indicating functionally related tissues that have abnormal activity levels, as determined from a population of patients having the associated behavioral disorder. Exemplary neural circuits are shown in FIG. 3 (depression), FIG. 7 (hyperphagia and/or obesity), FIG. 8 (addiction), and FIG. 9 (OCD). One or more candidate anatomical target corresponding with the behavior is identified 108 in the context of the surrounding anatomy using the identified neural circuit 106 and/or the data from imaging 104. The imaging data may be used to verify, tailor, and or modify the candidate target 110. For example, the depression circuit 130 of FIG. 3 may be identified in response to a clinical diagnosis of depression within the DSM IV criteria, and imaging of the patient's brain may verify hyperactivity of Cg25, indicating this is a suitable candidate target. The anatomical boundaries of the target tissue (Cg25 in our example) for the patient may also be identified using the imaging data.

In step 112, a cellurlarly sublethal radiation dose is selected. Unlike traditional ablative radiosurgery dosing, the goal in many embodiments of the present invention is explicitly to not destroy the brain tissue effected, but rather to simply lower its reactivity, metabolic activity, and/or spontaneous firing rate. For example, a dose of 60 Gy may be prescribed to the target volume, with a maximum dose at any point of 75 Gy during one treatment stage. The selected dose should be sublethal to neurons, but effective in lowering their activity.

Figure 5:
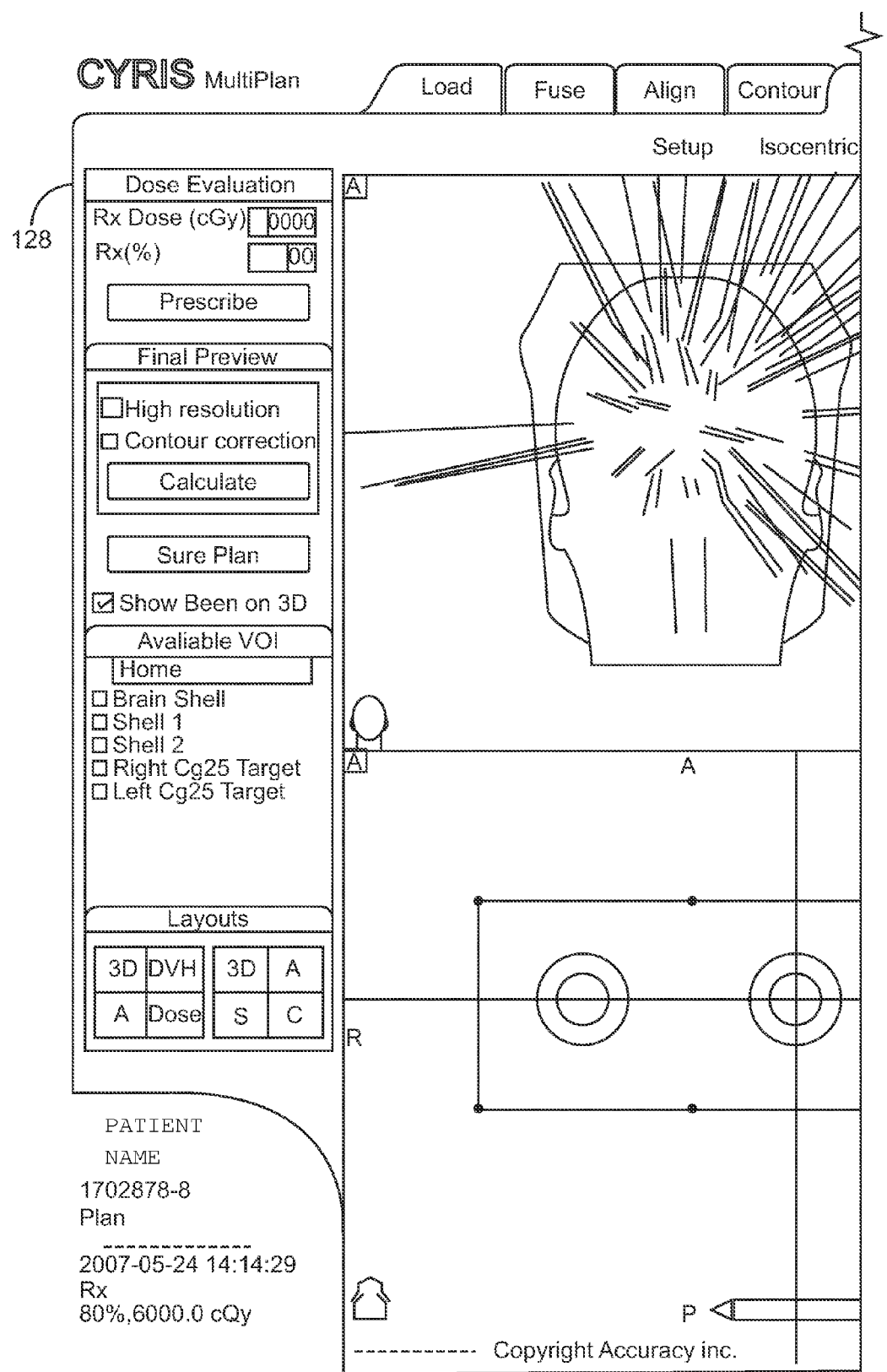
FIG. 5 illustrates a screen print from a planning module included in a processing system of the system of FIG. 1 for implementing a treatment according to embodiments of the invention.
Figure 5:
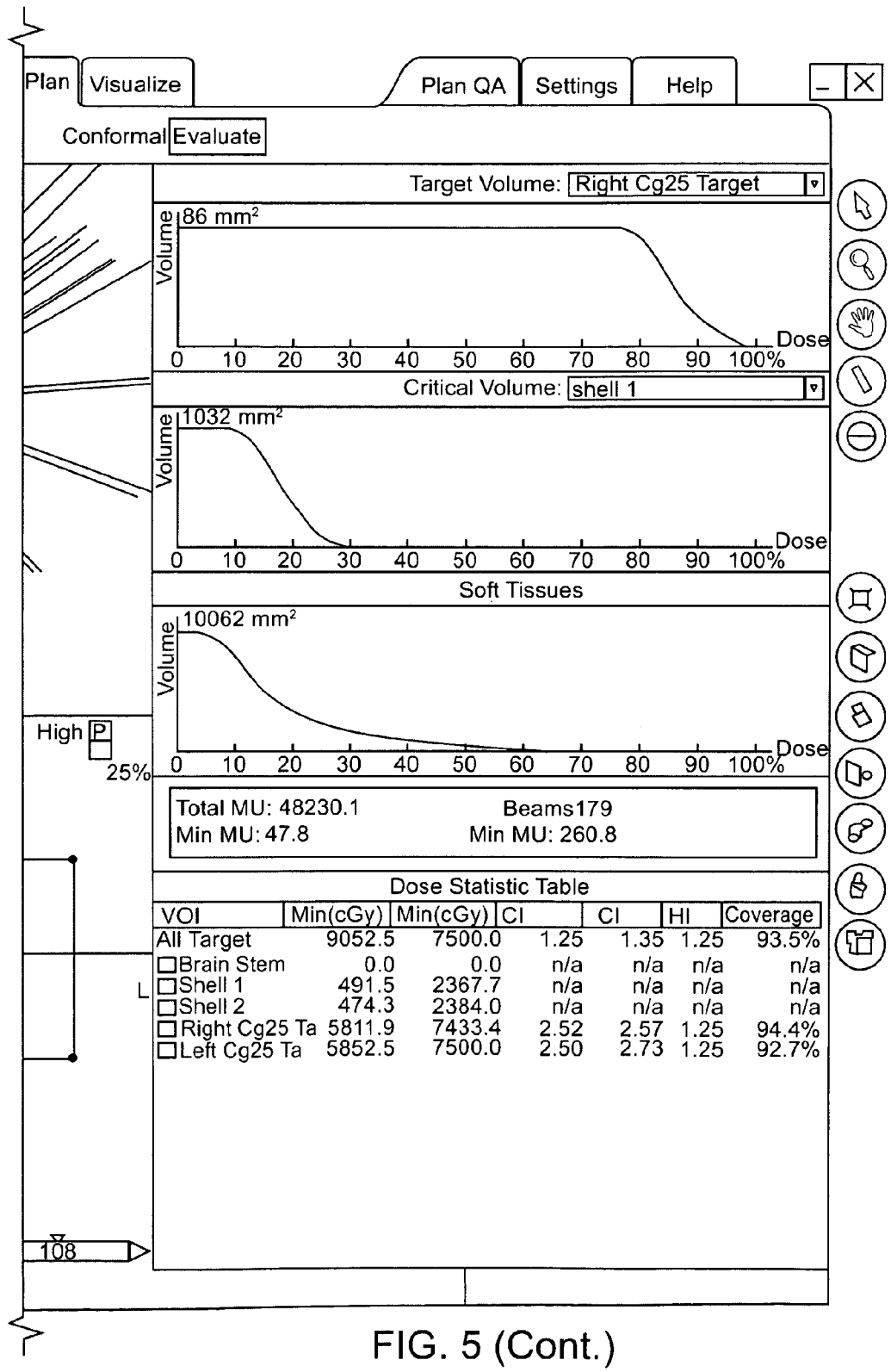

In step 114, preferably using a fused data set of each patient, the radiation treatment is planned. The Cyberknife™ treatment planning interface (or a modified version thereof), may, for example, be used to delineate, an approximately 5 mm$^3$ target volume within the subgenual cingulute. Referring to FIGS. 2 and 5, a screen print 128 of the Cyberknife™ treatment planning interface shows how the system facilitates planning of beam trajectories. The planning system should algorithmically seeks to achieve a steep dose gradient in the immediately surrounding brain. The radiosurgical platform will then compute a set of beam delivery trajectories in order to achieve the prescribed dose. These planning steps will often be performed on a separate computer circuit than that used to control the robot and activate the radiation source, with these separate data processing structures herein being referred to as elements of processing system 18.

The completed plan will be loaded into the treatment circuitry of the radiosurgical platform, for example a Cyberknife system, and the radiomodulation procedure will be performed 116. In the CyberKnife treatment room the patient is positioned supine on the procedure table while immobilized in a custom molded mask. The patient will be registered with respect to the spatial coordinates of the Cyberknife system, using an x-ray camera/CT matching system. Once proper registration has been confirmed, radiation delivery proceeds in accordance with the treatment plan described above, for example, at 60 Gy (Dmax 75 Gy) is delivered to the Cg25 target. Because radiation effects manifest a significant time 118 after surgery, a tissue response time of at least a plurality of weeks will pass before evaluation of the effects of treatment 116 is complete. Tissue response times will often be at least a month, more typically being a plurality of months, and in exemplary embodiments, may be about 90 days, so that clinical evaluation 120 of the treatment occurs approximately 90 days following treatment.

In clinical evaluation of the patient 120, the patient is re-evaluated, and may have additional neuroimaging (step 104, repeated) done. Clinical evaluation and/or imaging endpoints may determined whether a second stage of RM treatment is warranted. Criteria for recommending an addition stage of RM may include insufficient clinical response to previous RM stages, absence of sufficient metabolic decrease (for example in Cg25), and/or absence of significant impairment of surrounding brain structures.

Referring now to FIG. 3, exemplary target neural tissues included in a neural circuit 130 associated with depression are identified using a schematic radiation source 210 and associated radiation beam 212 directed to the target tissues. The solid small arrows shown on this neural circuit diagram schematically illustrate reciprocal corticolimbic, limbic-paralimbic, and cingulate-cingulate connections. The dotted arrows illustrate cortico-striatial-thalamic pathways. The dashed arrows show potential action in which remission to depression occurs when there is inhibition of the overactive ventral regions and activation of the previously hypofunctioning dorsal areas. This effect may be facilitated by antidepressant action in the brain stem, hippocampus, and posterior cingulate gyrus. Candidate target tissues of neural circuit 130, as shown in FIG. 3, may include a dorsal anterior cingulate cortex dCg24; a rostral anterior cingulate cortex rCg24a; Cg32; and/or a subgenual cingulate cortex sCg25 (sometimes referred to herein as Brodmann's Area 25, a subgenual cingulate, or Cg25). An exemplary treatment for depression will, for example, comprise targeting of Cg25. Other tissues included in neural circuit 130 include dorsal prefrontal cortex or dorsolateral prefrontal cortex dFr9/46; parahippocampus-medial temporal ph-mT; premotor frontal cortex pmF6; pariental cortex or posterior insula Par40/plns; striatum-globus pallidus St-gp; thalamus thal; pons; hypothalamus hth; anterior insula A-Ins; hippocampus hc; parahippocampus or medial temporal lobe Ph-mT; and posterior cingulate cortex pCg23/31. Additional information regarding related neural circuits is available from a number of sources, including the publications of Helen Mayberg and other others.

Figure 4B:
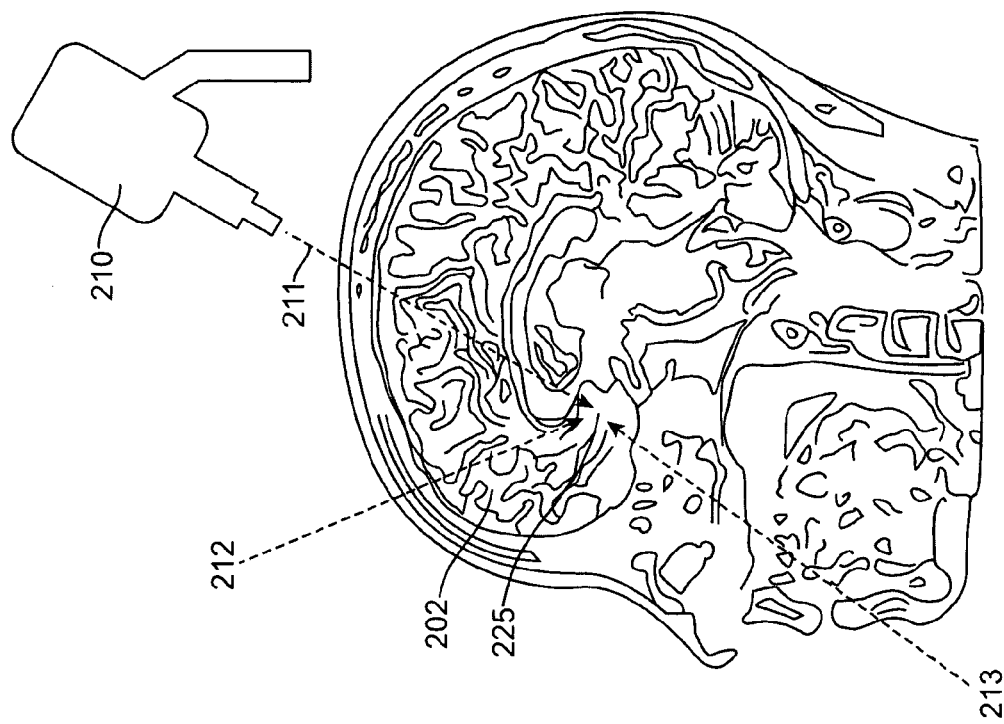
FIGS. 4A and 4B schematically illustrate a patient having target neural tissues at Cg25 irradiated for treatment of depression according to an embodiment of the invention.
Figure 4A:
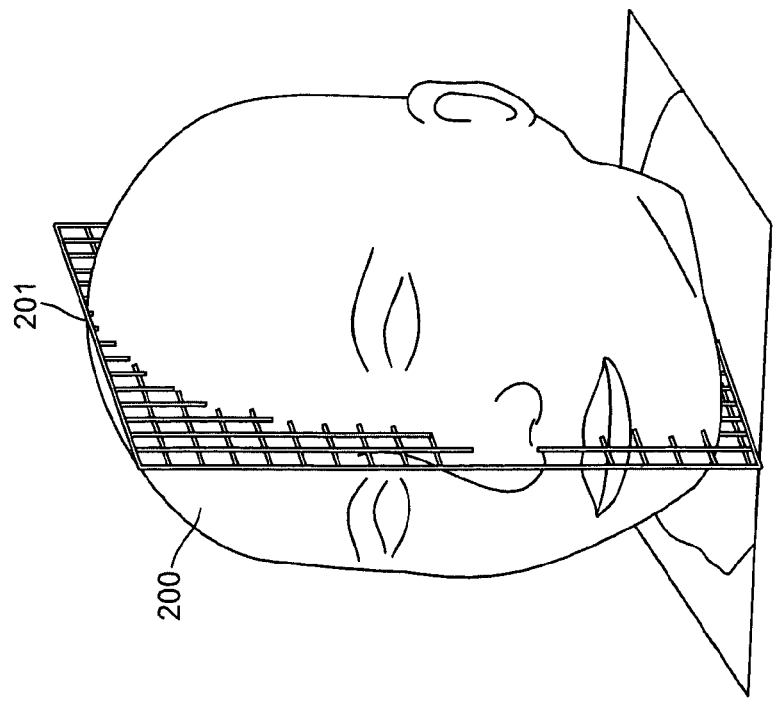

Referring now to FIGS. 4A and 4B, patient's head 200 is illustrated in cross-section along plane 201. Within brain 202, subgenual cingulate target 225 (Cg25) is visible. Radiation source 210 is schematically illustrated delivering a beam along trajectory 211, and will also be used (by robotically moving the source) to direct radiation along trajectory 212, and trajectory 214, all of which intersect at target 225. The total dose of radiation to be received by target 225 downwardly modulates target 225 reactivity, metabolic rate, and/or spontaneous firing rate, but does not tend to ablate or destroy the tissue (Cg25) within the target.

Referring to FIG. 5, a screen shot 128 of an interface for planning of a RN treatment for mitigation of a behavioral disorder per the system user input is shown. Screen shot 128 may also indicate gradients of radiation to which adjacent neural tissues are subjected, as well as the trajectories of radiation beams generated by the software. Tissues which are desired to have particularly limited radiation may also be identified by the input from the system user, so that the system calculates appropriate trajectories to limit collateral tissue damage of sensitive structures.

FIGS. 6A-6C and 7 illustrate a process by which obesity and/or hyperphagia may be treated and a neural circuit associated with obesity. In the exemplary method obesity and excessive eating disorders may be treated by radiomodulation of the lateral nuclei of the hypothalamus. The nuclei of the lateral hypothalamus, which comprises the lateral hypothalamic area, is a portion of the brain which creates the sensation of hunger. For example, when the blood sugar level declines, this message is relayed to the lateral hypothalamic area, which then causes a sensation of hunger to be felt. This feeling will continue until adequate glucose in the blood signals the ventromedial nuclei of the hypothalamus, which creates a sensation of satiety. Damage to the lateral hypothalamic area can lead to reduced food intake. High-frequency deep brain stimulation, which typically has an inhibitory effect upon stimulated structures, leads to a similar reduced appetite state. In this embodiment, obesity treatment may instead be provided using radiomodulation to the lateral nuclei of the hypothalamus, typically on each side of the brain.

Figure 6A:
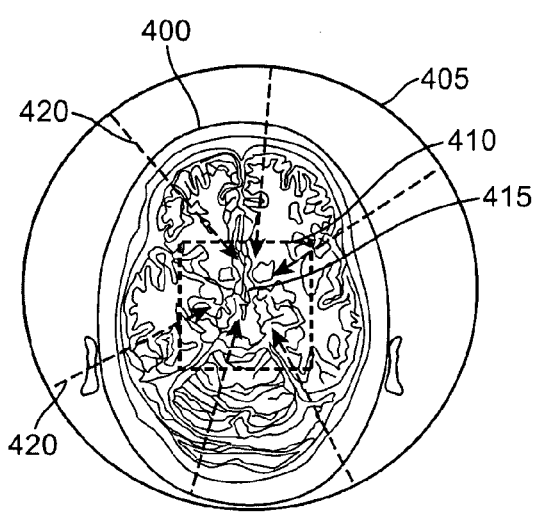
FIGS. 6A-6C graphically illustrate exemplary target neural tissues for treatment of obesity according to embodiments of the invention.
Figure 6B:
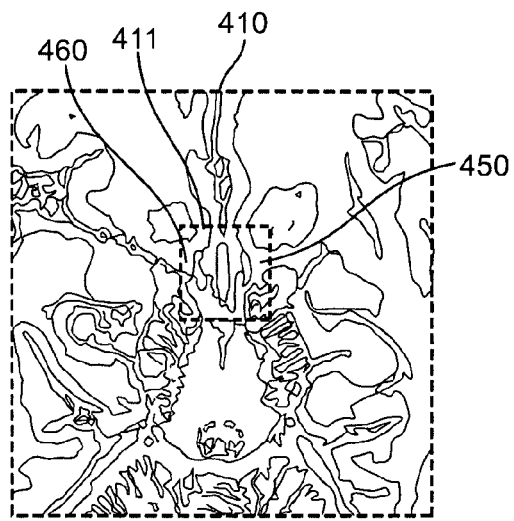
Figure 6C:
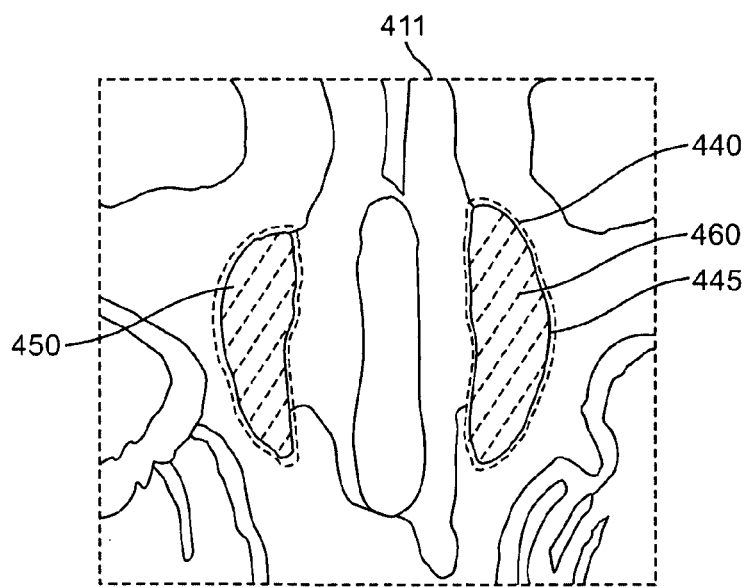

In FIG. 6A, patient 400 is treated with radiation beams 415 (representative example of other radiation beams, also illustrated as dotted lines with arrows). These radiation beams may come from any number of sources known in the art, including the Cyberknife (Accuray, Inc., Santa Clara, Calif.), or Gamma Knife 405 (Elekta, Stockholm, Sweden). Additionally, ion beam particle therapy may be utilized for this and the other treatments described herein (IBA, Belgium). Beams 420 are shown aimed at right lateral hypothalamic area 415, which lies within the dashed lines bounding region 410. FIGS. 6B and 6C illustrates an intermediate 410 view and a closeup view 411 of the region, respectively. The target here includes both the right lateral hypothalamic area 450, and left lateral hypothalamic nucleus 460, both nuclei shaded in the diagrams for illustrative purposes. The desired radiomodulation effects may be achieved, for example, by delivering a dose such as 60 Grey of radiation to each of those targets, with subsequent fractions delivered as needed. A steep gradient 440 adjacent the anatomical boundaries 445 of the target neural tissues limits collateral damage to adjacent tissues.

Figure 7:
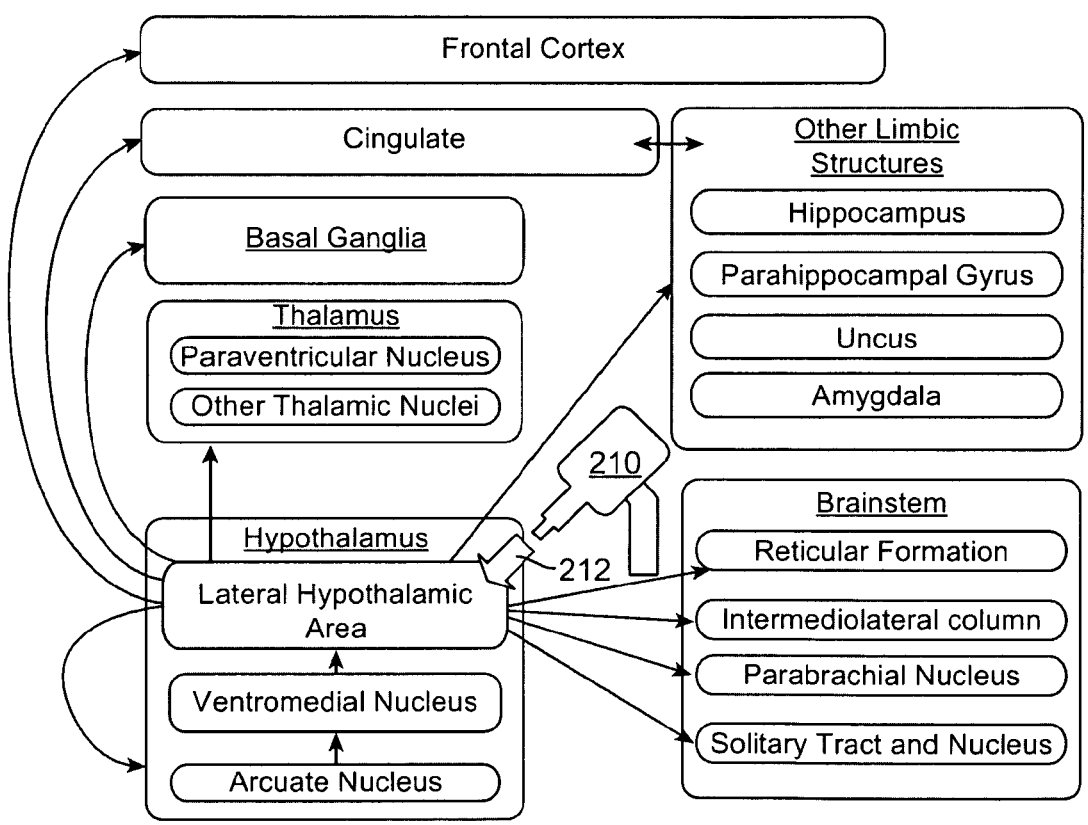
FIGS. 7, 8, and 9 schematically illustrate neural circuits associated with hyperphagia or obesity, addiction, and OCD, respectively, along candidate target tissues for treatment of each of these behavioral disorders according to embodiments of the present invention.
Figure 8:
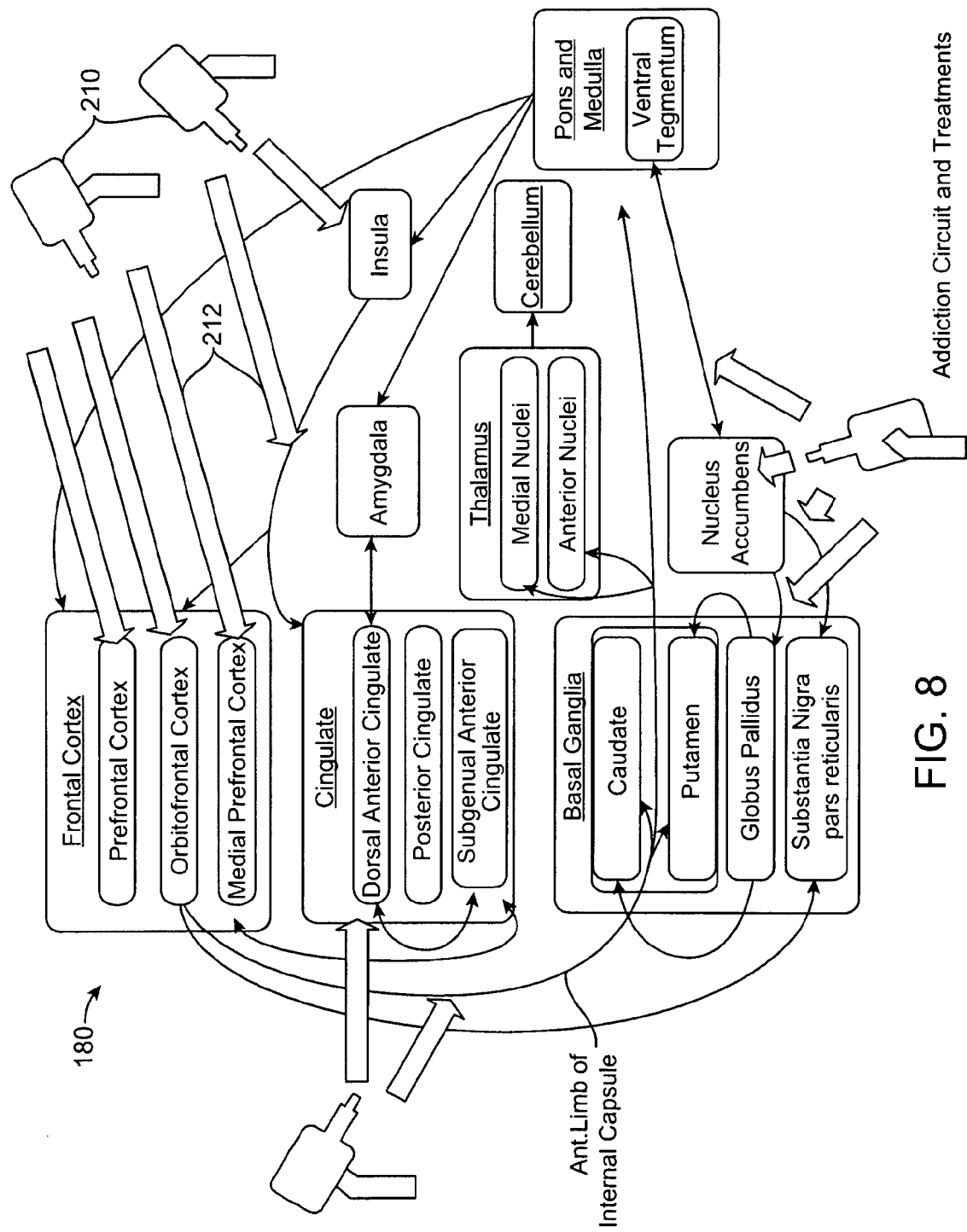
Figure 9:
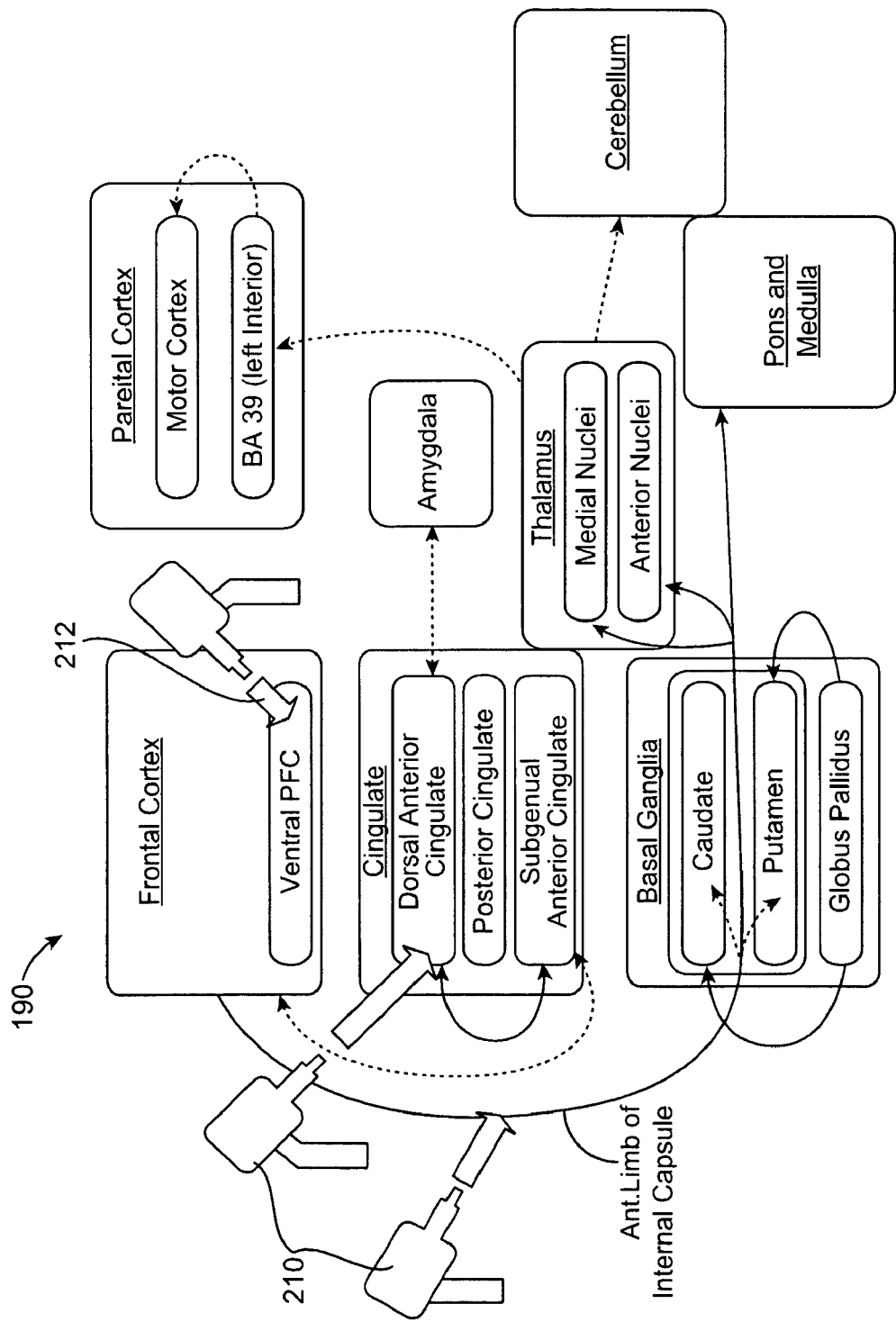

FIGS. 7-9 schematically illustrate neural circuits associated with hyperphagia or obesity, addiction, and OCD, respectively. First addressing FIG. 7, exemplary target neural tissues included in a neural circuit 170 associated with hunger and obesity are again identified using a schematic radiation source 210 and associated radiation beam 212 directed to the target tissues. The solid small arrows shown on this neural circuit diagram schematically illustrate neural connections. Candidate target tissues of neural circuit 170, as shown in FIG. 7, may include the lateral hypothalamic area, the portion of the brain which creates the sensation of hunger. Other tissues included in neural circuit 170 include the frontal cortex, cingulate, basal ganglia, the thalamaus, the paraventricular nucleus of the thalamus, other thalamic nuclei, the hypothalamus, the ventromedial nucleus of the hypothalamus, the arcuate nucleus of the hypothalamus, the brainstem, the reticular formation of the brain stem, the intermediolateral column of the brainstem, the parabrachial nucleus of the brainstem, the solidatry tract and nucleus of the brainstem, and other limbic structures including the hippocampus, the parahippocampal gyrus, the uncus and the amygdala.

Referring now to FIG. 8, exemplary target neural tissues included in a neural circuit 180 associated with addiction are again identified using a schematic radiation source 210 and associated radiation beam 212 directed to the target tissues. The solid small arrows shown on this neural circuit diagram schematically illustrate neural connections. Candidate target tissues of neural circuit 180, as shown in FIG. 8, may include the prefrontal cortex, orbitofrontal cortex, medial prefrontal cortex, the dorsal anterior cingulate, the insula, the neural connection between the insula and the cingulate, the anterior limb of the internal capsule, the nucleus accumbens, the neural connection between the nucleus accumbens and the ventral tegmentum, the neural connection between the nucleus accumbens and the substantia nigra pars reticularis and the neural connection between the nucleus accumbens and the globus pallidus. Other tissues included in neural circuit 180 include the posterior cingulate, the subgenual anterior cingulate, the amygdala, the thalamus, the medial nuclei of the thalamus, the anterior nuclei of the thalamus, the cerebellum, the pons, the medulla, the ventral tegmentum and the basal ganglia, including the caudate, the putamen, the globus pallidus and the substantia nigra pars reticularis.

Referring now to FIG. 9, exemplary target neural tissues included in a neural circuit 190 with Obsessive-Compulsive Disorder (OCD) are once again identified using a schematic radiation source 210 and associated radiation beam 212 directed to the target tissues. The solid small arrows shown on this neural circuit diagram schematically illustrate known neural connections. The dashed arrows shown on this neural circuit diagram schematically illustrate hypothesized connections. Candidate target tissues of neural circuit 190, as shown in FIG. 9, may include the ventral prefrontal cortex (PFC), the dorsal anterior cingulate and the anterior limb of the internal capsule (Ant. Limb of Internal Capsule). Other tissues included in neural circuit 190 include the frontal cortex, the parietal cortex, the motor cortex, Brodmann area 39, the cingulate, the posterior cingulate, the subgenual anterior cingulate, the amygdala, the basal ganglia, the caudate of the basal ganglia, the putamen of the basal ganglia, the globus pallidus of the basal ganglia, the thalamus, the medial nuclei of the thalamus, the anterior nuclei of the thalamus, the cerebellum, the pons and medulla.

Figure 10:
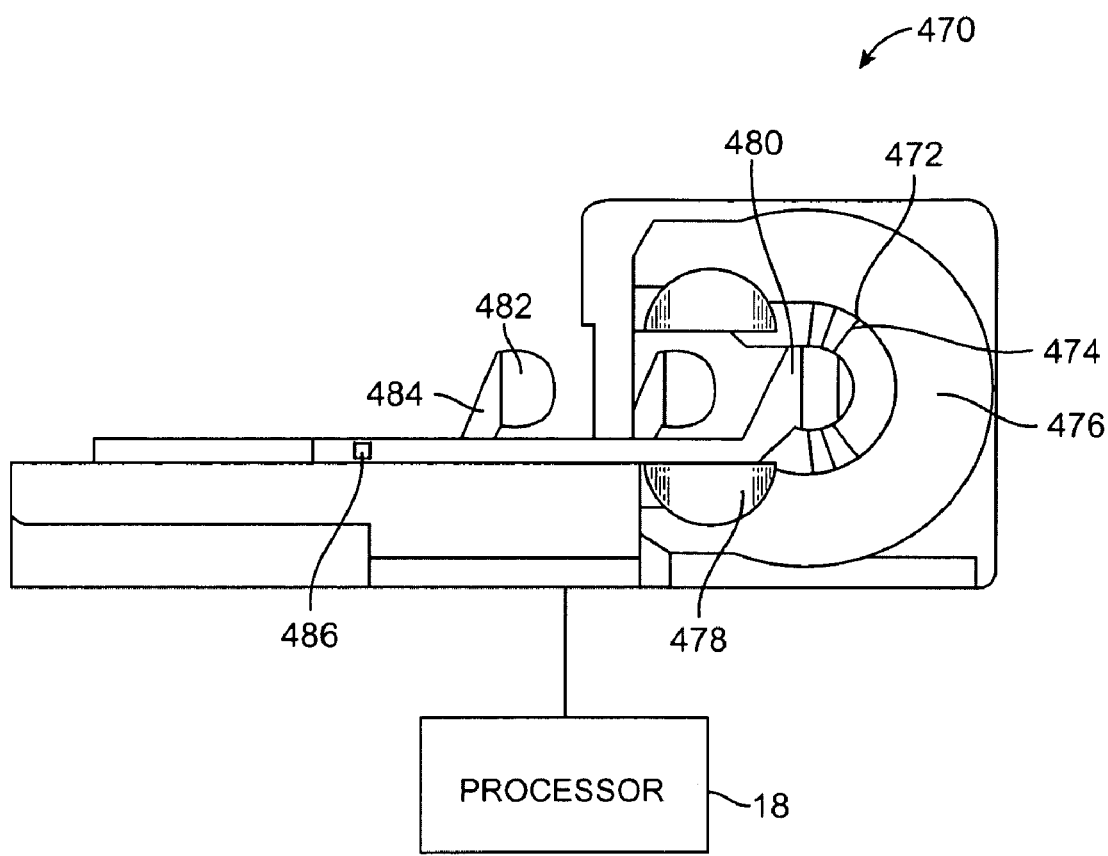
FIG. 10 schematically illustrates an alternative stereotactic radiosurgical system for implementing behavioral disorder treatments according to embodiments of the present invention.

Referring now to FIG. 10, radiosurgical systems having quite different structures may be employed in the treatments of behavioral disorders described herein. Here, a radiosurgical system 470 includes a radiation source having a spherical array of discrete cobalt 60 sources 472, with each source having an associated collimator 474 so as to direct a beam of radiation radially inwardly. Shielding 476 and doors 478 limit release of radiation, and an automated positioning system 480 helps position the target tissues at the center of the radiation beam trajectories. A helmet 482 is rigidly affixed to the head of the patient, and may include at least a portion of the collimators. The helmet is mounted to helmet supports 484, and the helmet and patient (on a movable treatment surface 486) are translated into alignment with the radiation source. Hence, at least some of the radiation beams may be delivered simultaneously, with the alignment and dosages again being determined by processing system 18.

Figure 11:
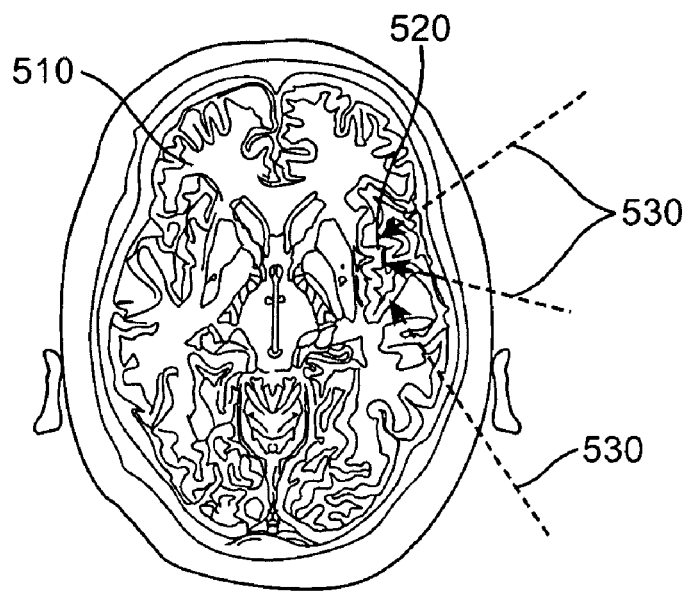
FIG. 11 schematically illustrates radiosurgical neuromodulation of the insula for treating addiction and/or other behavioral disorders.

A wide variety of behavioral disorders and conditions may be treated using the systems and method described herein. FIG. 11 illustrates a method for treatment of addiction (for example nicotine addiction) by radiomodulation (in this exemplary embodiment by irradiation of the insula). Addiction is associated with a variety of brain functions, including reward and expectation, and the driving neuroanatomic sources of addiction may vary between individuals. A patient with brain 510 has a region known as the insula. After the specific site of metabolic abnormality within the insula has been localized (for example by cued-state PET or fMRI) that locus, insula target 520 may be treated. Representative sample radiation beams 530 are shown converging upon insula target 520. For example the desired radiomodulation effects may be achieved by delivering a dose such as 60 Grey of radiation to each of those targets, with subsequent fractions delivered as needed.

Alternative embodiments of radiomodulation methods for treatment of addiction may also be provided. For example, the nucleus accumbens and septum may be used to decrease drug craving in the context of addiction. In an alternative embodiment, radiomodulation of hypermetabolic activity observed at the genu of the anterior cingulate (BA32) can be used to decrease drug craving. Alternatively, radiomodulation of the arcuate nucleus of the medial hypothalamus which contain peptide products of pro-opiomelanocortin (POMC) and cocaine-and-amphetamine-regulating transcript (CART) can also be used to decrease drug addiction behavior.

Figure 12:
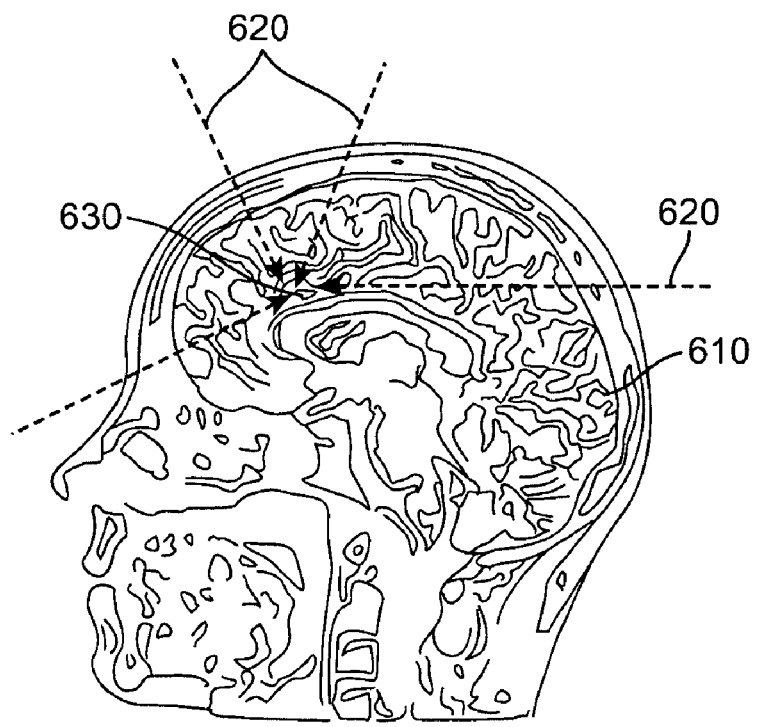
FIG. 12 schematically illustrates representative trajectories to effect radiosurgical neuromodulation of the dorsal anterior cingulate gyrus (Cg24, 32) for treating OCD, depression, and/or other behavioral disorders.

Additionally, addiction may be effectively treated by radiomodulation of the anterior cingulate cortex, also known as Brodmann's area 24. This same treatment is also effective for obsessive compulsive disorder. FIG. 12 illustrates the radiomodulation of the anterior cingulate cortex. Brain 610 includes anterior cingulate cortex target 630. Representative sample radiation beams 620 are shown converging upon anterior cingulate cortex target 630. The desired radiomodulation effects may be achieved, for example, by delivering a dose such as 60 Grey of radiation to each of those targets, with subsequent fractions delivered as needed.

Obsessive-Compulsive Disorder (OCD) may also be treated by radiomodulation treatments. Destructive lesions to the anterior capsule, and analogous DBS to that region are established means of treating severe, intractable OCD. Such approaches may be emulated (with less damage to the tissue, and potentially, less damage to higher cognitive functions) using radiomodulation to the anterior limb of the internal capsule, or alternatively, to regions such as BA32 and Cg24 (which show metabolic decrease as OCD remits). The desired radiomodulation effects may be achieved, for example, by delivering a dose such as 60 Grey of radiation to each of those targets, with subsequent fractions delivered as needed.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A method for treating a psychiatric behavioral disorder or hyperphagia of a patient, the behavioral disorder or hyperphagia associated with a level of neuronal activity in a neural circuit within a brain of the patient and provoking deleterious volitional behavior by the patient, the method comprising:
   transmitting a cellularly sub-lethal quantity of ionizing radiation from outside the patient into a target within the brain of the patient so as to alter the level of neuronal activity in the neural circuit such that the behavioral disorder or hyperphagia is mitigated, wherein the radiation is transmitted from a radiation source machine outside the patient, through a skull of the patient and into the brain of the patient along a plurality of beam paths directed from varying directions so as to intersect with the target; and
   performing a clinical evaluation indicating that the behavioral disorder or hyperphagia is mitigated.

2. The method of claim 1, wherein the neural circuit comprises a behavioral neural circuit associated with the behavioral disorder or hyperphagia, and wherein the overall functioning of the neural circuit is abnormal prior to the treatment.

3. The method of claim 2, wherein neural tissue within the target is morphologically normal prior to the treatment.

4. The method of claim 2, wherein the neural tissue within the target down-regulates the level of neuronal activity within at least a portion of the neural circuit, wherein the radiation decreases activity in the neural tissue so as to increase the level of neuronal activity within at least a portion of the neural circuit.

5. The method of claim 2, wherein the neural tissue within the target regulates the level of neuronal activity within at least a portion of the neural circuit, and wherein the radiation decreases activity in the neural tissue so as to change the neuronal activity within said at least a portion of the neural circuit.

6. The method of claim 1, wherein the sub-lethal quantity of radiation comprises, during a single treatment:
about 60 Gy when the target has a volume of about 0.05 cc;
less than about 60 Gy when the target has a volume of significantly more than about 0.05 cc; and/or
more than about 60 Gy when the target has a volume of significantly less than about 0.05 cc.

7. The method of claim 1, wherein the behavioral disorder comprises depression, and wherein the radiation mitigates the depression.

8. The method of claim 7, wherein the target comprises a rostral anterior cingulate; a dorsal anterior cingulate; and/or a subgenual cingulate.

9. The method of claim 1, wherein the behavioral disorder comprises Obsessive-Compulsive Disorder (OCD), and wherein the radiation mitigates the OCD.

10. The method of claim 9, wherein the target comprises an anterior limb of an internal capsule; a ventral PFC, and/or a dorsal anterior cingulate.

11. The method of claim 1, wherein the behavioral disorder comprises addiction, and wherein the radiation mitigates the addiction.

12. The method of claim 11, wherein the target comprises a region of an insula; a genu of the anterior cingulate; an arcuate nucleus of a medial hypothalamus; an anterior cingulate cortex; an orbitofrontal cortex; a medial prefrontal cortex; a dorsal anterior cinguate; an anterior limb of an internal capsule; a nucleus accumbens; and/or a neural circuit connection between the ventral tegmentum and the nucleus accumbens.

13. The method of claim 1, wherein the patient has hyperphagia, and wherein the radiation of the target mitigates the hyperphagia.

14. The method of claim 13, wherein the target comprises a lateral nucleus of a hypothalamus and/or bilateral nuclei of the hypothalamus.

15. The method of claim 1, wherein the radiation is transmitted from outside the patient so as to intersect with the target without accessing the target and/or the neural circuit.

16. The method of claim 1, further comprising planning the beam paths of the radiation so as to selectively apply the sub-lethal quantity of radiation to the target and to inhibit collateral damage to other tissues of the brain of the patient.

17. A method for treating a psychiatric behavioral disorder or hyperphagia of a patient, the behavioral disorder or hyperphagia associated with a level of neuronal activity in a neural circuit within a brain of the patient and provoking deleterious volitional behavior by the patient, the method comprising:
transmitting a cellularly sub-lethal quantity of ionizing radiation from a radiation source machine outside the patient, along a plurality of beam paths through a skull of the patient, and into a target within the brain of the patient so as to alter the level of neuronal activity in the neural circuit such that the behavioral disorder or hyperphagia is mitigated, wherein the neural circuit comprises a behavioral neural circuit associated with the behavioral disorder or hyperphagia, wherein the overall functioning of the neural circuit is abnormal prior to the treatment, wherein the neural tissue within the target is included within the neural circuit, and wherein the radiation down-regulates the level of neuronal activity within the neural tissue and decreases overall activity of the neural circuit; and
performing a clinical evaluation indicating that the behavioral disorder or hyperphagia is mitigated.

18. The method of claim 17, wherein the neural tissue within the target regulates the level of neuronal activity within a portion of the neural circuit, and wherein the radiation decreases activity in the neural tissue so as to decrease the neuronal activity within the portion of the neural circuit.

19. A method for treating a psychiatric behavioral disorder or hyperphagia of a patient, the behavioral disorder or hyperphagia associated with a level of neuronal activity in a neural circuit within a brain of the patient and provoking deleterious volitional behavior by the patient, the method comprising:
transmitting a sub-lethal quantity of ionizing radiation from a radiation source machine outside the patient into a target within the brain of the patient so as to alter the level of neuronal activity in the neural circuit such that the behavioral disorder or hyperphagia is mitigated, wherein the target comprises a discrete tissue structure of the brain having anatomical boundaries, wherein the ionizing radiation is transmitted from a radiation source machine as a plurality of radiation beams; and planning the radiation beams so that radiation outside the anatomical boundaries drops off sufficiently to inhibit collateral damage to adjacent neural tissues and preserve cognitive function.

20. The method of claim 19, wherein the target has a volume of less than 0.5 cc.

21. The method of claim 19, further comprising collimating at least some of the radiation beams to a beam cross-sectional size of less than 3 mm.

22. A method for treating a psychiatric behavioral disorder or hyperphagia of a patient, the behavioral disorder or hyperphagia associated with a level of neuronal activity in a neural circuit within a brain of the patient and provoking deleterious volitional behavior by the patient, the method comprising:
clinically determining that the behavioral disorder falls within an accepted psychiatric standard;
identifying a target within the brain of the patient using an accepted psychiatric neural circuit associated with the behavioral disorder; and
transmitting, after the clinical determination, a sub-lethal quantity of ionizing radiation from a radiation source machine outside the patient into the target so as to alter the level of neuronal activity in the neural circuit such that the behavioral disorder or hyperphagia is mitigated.

23. The method of claim 22, further comprising identifying or verifying the target by imaging localized neuronal activity levels along the neural circuit of the patient.

24. A method for treating a psychiatric behavioral disorder or hyperphagia of a patient, the behavioral disorder or hyperphagia associated with a level of neuronal activity in a neural circuit within a brain of the patient and provoking deleterious volitional behavior by the patient, the method comprising:
transmitting a sub-lethal quantity of ionizing radiation from a radiation source machine outside the patient into a target within the brain of the patient so as to alter the level of neuronal activity in the neural circuit such that the behavioral disorder or hyperphagia is mitigated; and
verifying mitigation of the behavioral disorder after a plurality of months, wherein the radiation alters the level of neuronal activity at least a plurality of weeks after the radiation is delivered to the target.

25. A method for treating Obsessive-Compulsive Disorder (OCD) of a patient, the OCD associated with a level of neuronal activity in a neural circuit within a brain of the patient and provoking deleterious volitional behavior by the patient, the method comprising:

transmitting a cellularly sub-lethal quantity of ionizing radiation from a radiation source machine outside the patient, along a plurality of beam paths through a skull of the patient, and into a target within the brain of the patient so as to alter the level of neuronal activity in the neural circuit such that the OCD is mitigated; and performing a clinical evaluation indicating that the OCD is mitigated;

wherein the target comprises an anterior limb of an internal capsule; BA32; Cg24; a ventral PFC, and/or a dorsal anterior cingulate.

26. A method for treating chronic depression of a patient, the method comprising:

transmitting a cellularly sub-lethal quantity of ionizing radiation from outside the patient, through a plurality of intermediate tissues, and into a target within the brain of the patient so as to alter neuronal activity, without surgically accessing the target, such that the depression is mitigated, wherein the radiation is transmitted from a radiation source machine outside the patient, through a skull of the patient and into the brain of the patient along a plurality of beam paths directed from varying directions so as to intersect with the target; and performing a clinical evaluation indicating that the depression is mitigated.

27. A method for treating Obsessive-Compulsive Disorder (OCD) of a patient, the method comprising:

transmitting a cellularly sub-lethal quantity of ionizing radiation from outside the patient, through a plurality of intermediate tissues, and into a target within the brain of the patient so as to alter neuronal activity, without surgically accessing the target, such that the OCD is mitigated, wherein the radiation is transmitted from a radiation source machine outside the patient, through a skull of the patient and into the brain of the patient along a plurality of beam paths directed from varying directions so as to intersect with the target; and performing a clinical evaluation indicating that the OCD is mitigated.

28. A method for treating addiction of a patient, the method comprising:

transmitting a cellularly sub-lethal quantity of ionizing radiation from outside the patient, through a plurality of intermediate tissues, and into a target within the brain of the patient so as to alter neuronal activity, without surgically accessing the target, such that the addiction is mitigated, wherein the radiation is transmitted from a radiation source machine outside the patient, through a skull of the patient and into the brain of the patient along a plurality of beam paths directed from varying directions so as to intersect with the target; and performing a clinical evaluation indicating that the addiction is mitigated.

29. A method for treating hyperphagia of a patient, the method comprising:

transmitting a cellularly sub-lethal quantity of ionizing radiation from outside the patient, through a plurality of intermediate tissues, and into a target within the brain of the patient so as to alter neuronal activity, without surgically accessing the target, such that the hyperphagia is mitigated, wherein the radiation is transmitted from a radiation source machine outside the patient, through a skull of the patient and into the brain of the patient along a plurality of beam paths directed from varying directions so as to intersect with the target; and performing a clinical evaluation indicating that the hyperphagia is mitigated.

30. A system for treating a psychiatric behavioral disorder or hyperphagia of a patient, the behavioral disorder associated with a level of neuronal activity in a neural circuit within a brain of the patient and provoking deleterious volitional behavior by the patient, the system comprising:

a source for transmitting ionizing radiation; and a processing system coupled to the source, the processing system configured to effect transmission of a plurality of beams of the radiation from the source into a target within the brain of the patient so that the radiation within the target is a cellularly sub-lethal quantity and is sufficient to alter the level of neuronal activity in the neural circuit such that the behavioral disorder or hyperphagia is mitigated, wherein the processing system comprises a non-transitory computer readable medium comprising software that causes the processing system to plan transmission of the plurality of beams so that the beams are transmitted from varying directions and intersect with the target, and so that radiation outside the target drops off sufficiently to inhibit collateral damage to other tissues of the brain.

31. The system of claim 30, wherein the software of the processing system is configured for planning transmission of the plurality of beams in response to input command signals received by an input, wherein the processing system transmits signals per the software so as to effect a desired positioning of the radiation beams relative to the target.

32. The system of claim 31, the target comprising a discrete tissue structure of the brain having anatomical boundaries, wherein, in use, the processing system plans the plurality of radiation beams from a plurality of beam source locations disposed outside the patient, and wherein the processing system plans the radiation beams so that radiation outside the anatomical boundaries drops off sufficiently to inhibit collateral damage to adjacent neural tissues and preserve cognitive function.

33. The system of claim 30, wherein the target has a volume of less than 0.5 cc.

34. The system of claim 33, wherein the source comprises a collimator disposed along a path of the radiation, the collimator collimating at least some of the radiation beams to a beam cross-sectional size of less than 3 mm at the target.

35. The system of claim 30, further comprising a neural circuit image capture device coupled to the processing system, the image capture device configured to generate image data comprising localized neuronal activity levels along the neural circuit, and wherein the software is configured to facilitate planning the beams in response to the image data.

36. The system of claim 35, wherein the image capture device comprises a positron emission tomography (PET) system, a single photon emission tomography (SPECT) system, and/or functional magnetic resonance imaging (fMRI) system.

37. The system of claim 30, wherein the processing system is configured so that the sub-lethal quantity of radiation comprises:

about 60 Gy during a single treatment when the target has a size of about 0.05 cc;

less than about 60 Gy when the target has a size of significantly more than about 0.05 cc; and/or more than about 60 Gy when the target has a size of significantly less than about 0.05 cc.

38. The system of claim 30, wherein the behavioral disorder comprises depression, and wherein the radiation mitigates the depression.

39. The system of claim 38, wherein the target comprises a rostral anterior cingulate; a dorsal anterior cingulate; and/or a subgenual cingulate of the brain.

40. The system of claim 30, wherein the behavioral disorder comprises Obsessive-Compulsive Disorder (OCD), and wherein the radiation mitigates the OCD.

41. The system of claim 40, wherein the target comprises an anterior limb of an internal capsule; BA32; Cg24; a ventral PFC, and/or a dorsal anterior cingulate.

42. The system of claim 40, wherein the target comprises an anterior limb of an internal capsule; a ventral PFC, and/or a dorsal anterior cingulate.

43. The system of claim 30, wherein the behavioral disorder comprises addiction, and wherein the radiation mitigates the addiction.

44. The system of claim 43, wherein the target comprises a region of an insula; a genu of the anterior cingulate; an arcuate nucleus of a medial hypothalamus; anterior cingulate cortex; an orbitofrontal cortex; a medial prefrontal cortex, a dorsal anterior cinguate; an anterior limb of an internal capsule; a nucleus accumbens; and/or a neural circuit connection between the ventral tegmentum and the nucleus accumbens.

45. The system of claim 30, wherein the patient has hyperphagia, and wherein the radiation of the target mitigates the hyperphagia.

46. The system of claim 45, wherein the target comprises a lateral nucleus of a hypothalamus and/or bilateral nuclei of the hypothalamus.

47. The system of claim 30, wherein the source comprises a plurality of cobalt 60 sources distributed generally spherically and an associated plurality of collimators oriented generally radially inwardly.

48. The system of claim 30, wherein the source comprises a linear accelerator.

49. The system of claim 30, wherein the processing system is configured to generate a sequence of beams, and further comprising:
    a robot coupled to the processing system and supporting the source so as to robotically re-position the source and orient sequential beams toward the target tissue; and
    a plurality of treatment image capture devices coupled to the processing system for transmitting registration images of the patient during treatment, the processing system having a patient registration module for aligning the radiation with the patient in three dimensions in response to the registration images.

\* \* \* \* \*